(12) United States Patent
Kram et al.

(10) Patent No.: US 8,512,978 B2
(45) Date of Patent: Aug. 20, 2013

(54) METHODS AND COMPOSITIONS FOR A MICROEMULSION-BASED TISSUE TREATMENT

(71) Applicants: Brian H. Kram, Tucson, AZ (US); Christopher Bieniarz, Tucson, AZ (US); Paul D. Drumheller, Flagstaff, AZ (US)

(72) Inventors: Brian H. Kram, Tucson, AZ (US); Christopher Bieniarz, Tucson, AZ (US); Paul D. Drumheller, Flagstaff, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 13/644,655

(22) Filed: Oct. 4, 2012

(65) Prior Publication Data

US 2013/0029376 A1 Jan. 31, 2013

Related U.S. Application Data

(60) Continuation of application No. 12/165,020, filed on Jun. 30, 2008, now Pat. No. 8,288,121, which is a division of application No. 11/284,397, filed on Nov. 18, 2005, now abandoned.

(60) Provisional application No. 60/636,942, filed on Dec. 17, 2004.

(51) Int. Cl.
*G01N 1/30* (2006.01)
*C12Q 1/00* (2006.01)
*B01F 3/00* (2006.01)

(52) U.S. Cl.
USPC ............... 435/40.52; 435/4; 435/40.5; 516/9

(58) Field of Classification Search
None
See application file for complete search history.

(56) References Cited

U.S. PATENT DOCUMENTS

| | | |
|---|---|---|
| 2,681,298 A | 6/1954 | Ferrari |
| 3,546,334 A | 12/1970 | Lerner et al. |
| 3,624,197 A | 11/1971 | Schain |
| 3,761,401 A | 9/1973 | Coleman, Jr. et al. |
| 4,161,460 A | 7/1979 | Sewell |
| 4,302,480 A | 11/1981 | Fischer et al. |
| 4,402,708 A | 9/1983 | Oswald |
| 4,404,181 A | 9/1983 | Mauthner |
| 4,446,044 A | 5/1984 | Rutkiewic et al. |
| 4,526,586 A | 7/1985 | Schwab et al. |
| 4,557,734 A | 12/1985 | Schwab et al. |
| 4,946,669 A | 8/1990 | Siegfried et al. |
| 5,106,730 A | 4/1992 | Van Ness et al. |
| 5,124,444 A | 6/1992 | Van Ness et al. |
| 5,130,238 A | 7/1992 | Malek et al. |
| 5,219,560 A | 6/1993 | Suzuki et al. |
| 5,492,837 A | 2/1996 | Naser-Kolahzadeh et al. |
| 5,521,061 A | 5/1996 | Bresser et al. |
| 5,552,087 A | 9/1996 | Zeheb et al. |
| 5,856,289 A | 1/1999 | Kennedy |
| 6,086,663 A | 7/2000 | Kondo et al. |
| 6,143,512 A | 11/2000 | Markovic et al. |
| 6,207,408 B1 | 3/2001 | Essenfeld et al. |
| 6,255,393 B1 | 7/2001 | Nikaya et al. |
| 6,337,189 B1 | 1/2002 | Ryan |
| 6,451,551 B1 | 9/2002 | Zhan et al. |
| 6,544,798 B1 | 4/2003 | Christensen et al. |
| 6,632,598 B1 | 10/2003 | Zhang et al. |
| 6,649,368 B1 | 11/2003 | Aghassi et al. |
| 6,709,836 B2 | 3/2004 | Kieftenbeld |
| 6,916,608 B2 | 7/2005 | Berger et al. |
| 6,953,507 B2 | 10/2005 | Kravitz et al. |
| 7,186,522 B2 | 3/2007 | Lapen et al. |
| 2002/0148573 A1 | 10/2002 | Freeland |
| 2003/0049172 A1 | 3/2003 | Thiem |
| 2003/0175852 A1 | 9/2003 | Kalra et al. |
| 2004/0002163 A1 | 1/2004 | Reinhardt et al. |
| 2005/0090017 A1 | 4/2005 | Morales |
| 2005/0142631 A1 | 6/2005 | Mosconi et al. |
| 2005/1816114 | 8/2005 | Reinhardt et al. |
| 2005/0250211 A1 | 11/2005 | Reinhardt et al. |
| 2006/0134732 A1 | 6/2006 | Kram et al. |
| 2007/0172911 A1* | 7/2007 | Farrell et al. ................. 435/40.5 |
| 2007/0269390 A1 | 11/2007 | Inoue |

FOREIGN PATENT DOCUMENTS

| | | |
|---|---|---|
| EP | 0908534 A1 | 4/1999 |
| JP | 08041263 A | 2/1996 |
| JP | 10054942 A | 2/1998 |
| JP | 2002239482 A | 8/2002 |
| WO | WO 9716731 A1 | 9/1997 |
| WO | 99/63342 | 12/1999 |
| WO | 0014507 A1 | 3/2000 |
| WO | 2004086001 A1 | 10/2004 |

OTHER PUBLICATIONS

Cui, Z and Mumper, R J "Plasmid DNA-Entrapped Nanoparticles Engineered from Microemulsion Precursors: in vitro and in vivo Evaluation" Bioconjugate Chem. 2002, 13(6), pp. 1319-1327.*

Ahel, M., et al, "Partitioning of Alkylphenois and Alkylphenol Polyethoxylates Between Water and Organic Solvents," Chemosphere, vol. 26, No. 8, p. 1471-1478 (1993).

Alany, R.G., et al, "Effects of Alcohols and Diols of the Phase Behaviour of Quarternary Systems," International Journal of Pharmecutics, vol. 196, p. 141-145 (2000).

Attwood, D., et al, "A Study on Factors Influencing the Droplet Size in Nonionic Oil-in-Water Microemulsions," International J. of Pharmecutics, vol. 88, p. 417-422 (1992).

(Continued)

*Primary Examiner* — Chris R Tate
*Assistant Examiner* — Aaron J Kosar
(74) *Attorney, Agent, or Firm* — Ventana Medical Systems, Inc.

(57) ABSTRACT

The invention is directed to methods and compositions for deparaffinizing paraffin-embedded biological samples for subsequent tissue staining. The compositions are microemulsions that may include water/oil/surfactant microemulsions, and optionally a cosurfactant. The microemulsions enable deparaffinization without the use of xylene or toluene, and also enable solvent exchange without the use of intermediary alcohol dehydration or alcohol rehydration compositions.

16 Claims, No Drawings

(56) References Cited

OTHER PUBLICATIONS

Attwood, D., "Microemulsions, in Kreuter H (ed): Colloidal Drug Delivery Systems," p. 31-71 (1994), Marcel Decker, New York.
Baviere, M., et al, "The Influence of Alcohols on Microemulsion Composition," J. Colloid Interface Science, vol. 81, No. 1, p. 266-279 (May 1981).
Gursoy, R.N., et al, "Self-emulsifying Drug Delivery Systems (SEDDS) for Improved Oral Delivery of Lipophilic Drugs," Biomedicine & Pharmacotherapy, vol. 58, p. 173-182 (2004).
Hoar, T.P., et al, "Transparent Water-In-Oil Dispersions: The Oleopathic Hydro-Micelle," Nature, vol. 152, p. 102-103 (Jul. 24, 1943).
Jayakrishnan, A., et al, "Microemulsions: Evolving Technologies for Cosmetic Applications," J. Soc. Cosmet. Chem., vol. 34, p. 335-350 (Nov. 1983).
Johnson, K.A., et al, "Effect of Oil Chain Length and Electrolytes on Water Solubilization in Alcohol-Free Pharmecutical Microemulsions," J. Colloid Interface Science, vol. 107, No. 1, p. 269-271 (Sep. 1985).
Johnson, K.A., et al, "Formulation and Properties of an Alcohol-Free, Pharmaceutical Microemulsion System," Surfactants in Solution, vol. 6, p. 1441-1456 (1986).
Kang, B.K., et al, "Development of Self-Microemulsifying Drug Delivery Systems (SMEDDS) for Oral Bioavailability Enhancement of Simvastatin in Beagle Dogs," International Journal of Pharmecutics, vol. 274, p. 65-73 (2004).
Keiser, B.A., et al, "Detergentless Water/Oil Microemulsions Composed of Hexane, Water and 2-Propanol. 2 Nuclear Magnetic Resonance Studies, Effect of Added NaC11" Journal of Physical Chemistry, vol. 83, No. 10, p. 1276-1280 (1979).
Khmelnitsky, Y.L., et al, "Detergentless Microemulsions, A New Microheterogenous Medium for Enzymatic Reaction," Ann NY Academy of Science, vol. 501, p. 161-165 (1987).
Khmelnitsky, Y.L., et al, "Detergentless Microemulsions as Media for Enzymatic Reactions Cholesterol Oxidation Catalyzed by Cholesterol Oxidase," Eur. J. Biochem., vol. 176, p. 265-217 (1988).
Little, R.C., "Correlation of Surfactant Hydrophile-Lipophile Balance (HLB) with Solubility Parameter," J. Colloid & Interface Science, vol. 65, No. 3, p. 587-588 (Jul. 1978).
Lohateeraparp, P., et al, "Study of Alcohol-free Micremulsion Systems Containing Fatty Acids as Cosurfactants," Journal of Surfactants and Detergents, vol. 6, No. 1, p. 15-24 (Jan. 2003).
Mullin, L.S., et al, "Toxicology Update Isoparaffinic Hydrocarbons: A Summary of Physical Properties, Toxicity Studies and Human Exposure Data," Journal of Applied Toxicology, vol. 10, No. 2, p. 135-142 (1990).
Nandi, I, et al, "Study of Isopropyl Myristate Microemulsion Systems Containing Cyclodextrins to Improve the Solubility of 2 Model Hydrophobic Drugs," AAPS PharmSciTech, vol. 4, No. 1 Article 10, 9 pages (2003).
Ogino, K, et al, "Microemulsion Formulation with some Typical Surfactants," Matijevic E. (ed): Surface and Colloid Science vol. 15, p. 85-123 (1993), Plenum Press, New York.
Paul, B.K., et al, "Microemulsions: An Overview," J. Dispersion Science & Technology, vol. 18, No. 4, p. 301-367 (1997).
Paul, B.K., et al, "Uses and Applications of Microemulsions," Current Science, vol. 80, No. 8, p. 990-1001 (Apr. 25, 2001).
Prince, L.M., "Microemulsions," J.Soc. Cosmetic Chem, vol. 21, p. 193-204 (Mar. 4, 1970).
Schott, H., "Solubility Parameter and Hydrophilic-Lipohilic Balance of Nonionic Surfactants," J. of Pharmaceutical Sciences, vol. 73, No. 6, p. 790-792 (Jun. 1984).
Smith, G.D., et al, "Oil-Continuous Microemulsions Composed of Hexane, Water and 2-Propanol," Journal of Colloid and Interface Science, vol. 60, No. 3, p. 488-496 (Jul. 1977).
Tenjarla, S., "Microemulsions: An Overview and Pharmaceutical Applications," Critical Reviews in Therapeutic Drug Carrier Systems, vol. 16, No. 5, p. 461-521 (1999).

Yuan, S., et al, "Quantitative Structure-property Relationships of Surfactants: Prediction of the Critical Micelle Concentration of Nonionic Surfactants," Colloid Polym. Sci., vol. 280, p. 630-636 (2002).
Prince, L.M., "Microemulsions, Theory and Practice," New York, Academic Press (1977), Table of Contents, pp. vii-viii.
"Emulsions, Latices, and Dispersions," edited by Paul Becher, p. 201-221, (1978) Marcel Dekker, Inc., New York and Basel.
"Microemulsions" Brochure, ISP Corp., Oct. 3, 2005, 15 pages, http://www.iscorp.com/products/agchem/content/brochure/pdf. MicroBig.pdf.
"Surfactants, Their Abilities and Important Physico-Chemical Properties," Report, 54 pages (2002).
"Technical Problems Associated with in Vitro Toxicity Testing Systems," A Report of the CAAT Technical Workshop of May 17-18, 1989, Center for Alternatives for Animal Testing, Technical Report No. 1, edited by Frazier, J.M., et al, 5 pages.
AO-14-2 Brochure, Tomah Products, Inc. 3 pages (Jul. 3, 1996).
Quaternaries Brochure, Tomah Products, Inc., 3 pages (Apr. 23, 1998).
Tomadyne 100 and 102 Surfactants for Industrial Cleaning Applications Brochure, Tomah Products, Inc., 2 pages (Jan. 23, 2001).
Tomadol Ethoxylated Alcohols Brochure, Tomah Products, Inc., 2 pages (Nov. 21, 2001).
Tomadol 400, 600 and 900 Brochure, Tomah Products, Inc., 1 page (Apr. 13, 2004).
Ethoxylated Amines Brochure, Tomah Products, Inc., 4 pages (Oct. 2, 2002).
Key Benefits of Using Tomadyne dL Brochure, Tomah Products, Inc., 2 pages (2003).
Shah, "Macro-and Microemulsions Theory and Applications," American Chemical Society (1985), pp. vii-viii.
Flick, E.W., "Industrial Surfactants," Noyes Publications (1988), pp. ix-xliv.
Friberg, S.E., et al, "Microemulsions: Structure and Dynamics," CRC Press, Inc. (1987), Table of Contents, 1 page.
Larsson, K, et al, "Enzymatic Catalysis in Microemulsions," Biotechnology and Bioengineering, vol. 36, p. 135-141 (1990).
Sigma, "Tergitol", Catalogue of Biochemicals, Organic Compounds for Research, and Diagnostic Reagents, Sigma-Aldrich Chemical Company, p. 963 (1995).
Harris, Robert S.; Sherman, Henry; Jetter, Walter W., "Nutritional and pathological effects of sorbitan monolaurate, polyoxyethylene sorbitan monolaurate, polyoxyethylene monolaurate, and polyoxyethylene monostearate when fed to rats" Archives of Biochemistry and Biophysics, vol. 34, No. 2, p. 249-258 (Dec. 1951) (Abstract Only).
Exxonmobil, "NORPAR," Exxon Mobil Corporation, http://exxonmobilchemical.com/Public_Products/Fluids/Aliphatics/Worldwide/Grades_and Datasheets/Fluids Aliphatics_Norpar_Grades_WW.asp, 2002 (accessed online Jan. 28, 2008) p. 1-4.
Owen, Sonia "Material Data Safety Sheet: Polyethylene Glycol 400 Monolaurate," Spectrum Chemical (Gardena, CA) (Sep. 13, 2006), p. 1-6.
Buesa, R.J., "Mineral Oil: The Best Xylene Substitute for Tissue Processing Yet?" J. Histotechnology, 23 (2), p. 143-148 (2000).
Histology Lecture #14: Introduction to Tissue Processing. URL: http://histologycourse.com/Tissue%20Processing.pdf, online Feb. 1, 2001, accessed Aug. 5, 2011, 18 pages.
Allison et al, "Effects of Processing at 45 C on Staining," Biotechnic & Histochemistry, May 1998, vol. 73, No. 3, p. 128-136.
Aloisi et al, "Negative Birefringence of Damaged Muscle Fibres: A Useful Artefact in Paraffin Sections," Journal of Pathology and Bacteriology, Jul. 1960, vol. 80, p. 33-41.
Cooper et al, "The Employment of a Surface Agent in Histological Techniques," J. Sci. Technol., 1968, vol. 14, No. 2, p. 29-32.
Heslinga et al, "The Action of Histological Fixatives on Tissue Lipids, Comparison of the Action of Several Fixatives Using Paper Chromatography," Journal of Histochemistry and Cytochemistry, Sep. 1961, vol. 9, p. 572-577.
Lee et al, "Skin Permeation Enhancement of Tegafur by Ethanol/Panasate 800 or Ethanol/Water Binary Vehicle and Combined Effect of Fatty Acids and Fatty Alcohols," Journal of Pharmaceutical Sciences, Nov. 1993, vol. 82, No. 11, p. 1155-1159.

Maneta-Peyret et al, "Immunohistochemistry of lipids: Chemical fixatives have dramatic effects on the preservation of tissue lipids," The Histochemical Journal, Aug. 1999, vol. 31, No. 8, p. 541-547.

Menzies, "Paraffin-Beeswax-Stearic Acid: An Embedding Mass for Thin Sections," Stain Technology, Jul. 1962, vol. 37, p. 235-238.

Rainbow, "Improved Method for Softening Hard Tissue," Tissue Talk, 1981, vol. 1, No. 1, p. 6.

Roberts, "Iso-butanol saturated water: a simple procedure for increasing staining intensity of resin sections for light and electron microscopy," Journal of Microscopy Techniques, Aug. 2002, vol. 207, No. Pt 2, p. 97-107.

Sinha et al, "Permeation of Enhancers for Transdermal Drug Delivery," Drug Development and Industrial Pharmacy, 2000, vol. 26, No. 11, p. 1131-1140.

Tracy et al, "Lipid fixation for fat staining in paraffin sections applied to lesions of atherosclerosis," Virchows Archiv., 2004, vol. 445, No. 1, p. 22-26.

Wallington, "Artifacts in tissue sections," Medical Laboratory Sciences, 1979, vol. 36, p. 3-61.

Viktorov, I.V. and Proshin, S.S. "Use of Isopropyl Alcohol in Histological Assays: Dehydration of Tissue, Enbessing [Embedding] into Paraffin, and Processing of Paraffin Sections," Bull Exp. Biol. Med., Jul. 2003, 136(1) pp. 119-120.

\* cited by examiner

METHODS AND COMPOSITIONS FOR A MICROEMULSION-BASED TISSUE TREATMENT

RELATED APPLICATION DATA

This application is a continuation of U.S. patent application Ser. No. 12/165,020 filed Jun. 30, 2008 which is a Divisional of prior U.S. patent application Ser. No. 11/284,397, filed Nov. 18, 2005, and claims the benefit of U.S. Provisional Patent Application No. 60/636,942, filed Dec. 17, 2004, the contents of which are hereby incorporated by reference in their entireties.

BACKGROUND

1. Field of the Invention

The inventions described herein are directed to the general field of anatomical pathology, and particularly to the preparation of biological samples, specifically tissue sections, for subsequent staining with chemical, immunohistochemical or in situ hybridization-based compositions. The tissue preparation methods and compositions provide for novel deparaffinization and solvent exchange of fluids within tissues, thereby readying them for further or potentially simultaneous staining.

2. Description of Related Art

The analysis of biological tissue samples is a valuable diagnostic tool used by the pathologist to diagnose many illnesses including cancer and infectious diseases and by the medical researcher to obtain information about cellular structure.

In order to obtain information from a biological tissue sample it usually is necessary to perform a number of preliminary operations to prepare the sample for analysis. While there are many variations of the procedures to prepare tissue samples for testing, these variations may be considered refinements to adapt the process for individual tissues or because a particular technique is better suited to identify a specific chemical substance or biological marker within the tissue sample. However, the basic preparation techniques are essentially the same. Biological tissue samples may derive from solid tissue such as from a tissue biopsy or may derive from liquid-based preparations of cellular suspensions such as from a smear (e.g., PAP smear), bone marrow, or cellular suspension.

Typically such procedures may include the processing of the tissue by fixation, dehydration, infiltration and embedding in paraffin wax; mounting of the tissue on a glass slide and then staining the sample; labeling of the tissue through the detection of various constituents; grid analysis of tissue sections, e.g., by an electron microscope, or the growing of sample cells in culture dishes.

Depending on the analysis or testing to be done, a sample may have to undergo a number of preliminary steps or treatments or procedures before it is ready to be analyzed for its informational content. Typically the procedures are complex and time consuming, involving several tightly sequenced steps often utilizing expensive and/or toxic materials.

For example, a typical tissue sample may undergo an optical microscopic examination so that the relationship of various cells to each other may be determined or abnormalities may be uncovered. Thus, the tissue sample must be an extremely thin strip of tissue so that light may be transmitted therethrough. The average thickness of the tissue sample or slice (often referred to as a "section") is on the order of 2 to 10 micrometers (1 micrometer=$\frac{1}{1000}$th of a millimeter). Typically, a tissue sample is either frozen or fixed in a material (a fixative) which not only preserves the cellular structure but also stops any further enzymatic action which could result in the putrification or autolysis of the tissue.

After fixation, the tissue sample is then dehydrated by the removal of water from the sample through the use of increasing strengths of a water-miscible alcohol, typically ethanol. The alcohol then is replaced by a chemical, typically a nonpolar material, which mixes with paraffin wax or some other plastic substance impregnant which can permeate the tissue sample and give it a consistency suitable for the preparation of thin sections without disintegration or splitting. The process of removing the water, or aqueous-based solutions, and replacing it with a nonpolar material, such as a nonpolar organic solvent, is called "solvent exchange" because it involves the sequential exposure of the tissue to solvent solutions of varying proportions of water/alcohol/nonpolar organic solvent until the water in the tissue is exchanged with another fluid (or when embedding tissue, a semi-solid paraffin wax also commonly referred to as paraffin). Solvent exchange can be used in either direction, i.e., it is a 2-way process; such as the process of removing the water and replacing it with a nonpolar material, and the process of removing the nonpolar material and replacing it with water.

A microtome is then utilized to cut thin slices from the paraffin-embedded tissue sample. The slices may be on the order of 5 to 6 micrometers thick while the diameter may be on the order of 5000 to 20000 microns. The cut thin sections are floated on a water bath to spread or flatten the section. The section is then disposed on a glass slide usually measuring about 2.5 by 8 centimeters (1×3 inches).

The paraffin wax or other impregnant is then removed by solvent exchange, e.g., exposing the sample to a paraffin solvent such as xylene, toluene or limonene, the solvent then being removed by alcohol, and the alcohol removed by sequential alcohol/water mixtures of decreasing alcoholic concentrations, until eventually the tissue is once more infiltrated by water or aqueous solutions. The infiltration of the sample by water permits the staining of the cell constituents by water soluble chemical and immunochemical dyes. This process is known as a deparaffinizing process.

Certain aspects of the deparaffinizing process have been improved in recent years. Toxic paraffin solvents such as xylene and toluene are now replaceable with less toxic nonpolar organic solvents such as Terpene Oil (e.g. AMERICLEAR™, Baxter Healthcare Diagnostics, McGaw Park, Ill.), isoparaffinic hydrocarbons such as MICROCLEAR™ from Micron Diagnostics of Fairfax, Va., and HISTO-LENE™, a dewaxer that is 96% d-Limonene (Fronine Pty Ltd, Riverstone, New South Wales, Australia). New automated methods have also debuted. For example, Ventana Medical Systems' U.S. Pat. No. 6,544,798 describes an automated method of removing paraffin wax from tissue sections using only hot water with surfactant. The process relies on the physical partitioning of the liquefied paraffin from the tissue by taking advantage of the immiscibility of liquefied paraffin and hot water. The process is widely used on the BENCH-MARK® series of automated tissue stainers.

U.S. Pat. No. 6,632,598 (Zhang et al.) describes methods and compositions for deparaffinizing paraffin-embedded tissue. The method involves contacting a paraffin wax-embedded specimen with a dewaxing composition to solubilize the wax impregnating the specimen prior to histochemical analysis. The dewaxing compositions specifically include a paraffin-solubilizing organic solvent selected from the group consisting of aromatic hydrocarbons, terpenes and isoparaffinic hydrocarbons, a polar organic solvent, and a surfactant to solubilize the wax associated with the specimen. Compositions can further comprise water. A cited advantage of the compositions is that they do not require xylene, toluene or similar undesirable paraffin solvents. However, the actual compositions all require large amounts of polar organic solvent, typically a water-miscible alcohol.

There remains a need for improved tissue preparation processes that do not require toxic or hazardous chemicals, and methods that decrease the time and steps involved in treating tissue samples to render them acceptable for tissue staining operations.

SUMMARY OF THE INVENTION

The invention is directed to a method of removing paraffin-based embedding medium from a paraffin-embedded biological sample comprising contacting the paraffin-embedded biological sample with a deparaffinizing microemulsion comprising surfactant, nonpolar organic solvent and water, wherein the surfactant is soluble in both the water and the nonpolar organic solvent, thereby transferring the paraffin to the microemulsion; and removing the microemulsion. It is preferable that the surfactant be individually soluble in both the nonpolar organic solvent and the water.

The invention is also directed to a method of preparing a paraffin-embedded biological sample for staining comprising deparaffinizing the paraffin-embedded biological sample by dissolving the paraffin with a nonpolar organic solvent; and exchanging the nonpolar organic solvent in the deparaffinized tissue with a microemulsion comprising surfactant, nonpolar organic solvent and water wherein the surfactant is soluble in both the water and the nonpolar organic solvent, also referred to as oil. An oil-in-water microemulsion is preferred, with a large amount of a surfactant. It is preferred that the surfactant be soluble in both the oil and the water.

The invention is also directed to a method of preparing a paraffin-embedded biological sample for staining comprising deparaffinizing the paraffin-embedded biological sample by dissolving the paraffin with a nonpolar organic solvent; and exchanging the nonpolar organic solvent in the deparaffinized tissue with a microemulsion comprising surfactant, nonpolar organic solvent, water, and polar organic cosurfactant wherein the surfactant is soluble in both the water and the nonpolar organic solvent.

DESCRIPTION OF THE PREFERRED EMBODIMENTS

The invention is directed to three distinct embodiments. The first embodiment is a method of removing paraffin-based embedding medium from a paraffin-embedded biological sample comprising contacting the paraffin-embedded biological sample with a deparaffinizing microemulsion comprising surfactant, nonpolar organic solvent and water, wherein the surfactant is soluble in both the water and the nonpolar organic solvent, thereby transferring the paraffin to the microemulsion; and then removing the microemulsion. The microemulsion composition is a ternary composition of surfactant, nonpolar organic solvent and water. Nonionic surfactants are preferred as they do not complicate later staining procedures that use ionic stains. One preferred composition comprises a 4:1:1 wt/wt composition of surfactant:oil:water.

The second embodiment is directed to a method of preparing a paraffin-embedded biological sample for staining comprising deparaffinizing the paraffin-embedded biological sample by dissolving the paraffin with a nonpolar organic solvent; and then exchanging the nonpolar organic solvent in the deparaffinized tissue with a microemulsion comprising surfactant, nonpolar organic solvent and water wherein the surfactant is soluble in both the water and the nonpolar organic solvent. The first deparaffinizing step ensures the paraffin-embedding medium is removed from the tissue. The following exchanging step replaces the nonpolar organic solvent with a microemulsion that is suitable for holding the tissue in stasis until the next step. In a subsequent step, the microemulsion can be replaced with either a water- or oil-based liquid. This embodiment allows the histotechnologist to create a staining procedure without using an intermediary alcohol rinse. The advantages of this embodiment are significant, including no alcohol waste and decreased expense. Also, the process eliminates the multiple-step prior art practice of alcohol gradations when practicing solvent exchange.

The third embodiment is directed to a method of preparing a paraffin-embedded biological sample for staining comprising deparaffinizing the paraffin-embedded biological sample by dissolving the paraffin with a nonpolar organic solvent; and then exchanging the nonpolar organic solvent in the deparaffinized tissue with a microemulsion comprising surfactant, nonpolar organic solvent, water, and polar organic cosurfactant wherein the surfactant is soluble in both the water and the nonpolar organic solvent. The main difference from the second embodiment is that the deparaffinizing composition additionally includes a polar organic cosurfactant such as typically an alcohol, a diol, or a glycol.

A "microemulsion" is normally composed of oil, water, surfactant, and cosurfactant.[1-5] Hoar and Schulman[6] were the first to introduce the word microemulsion, which they defined as a transparent solution obtained by titrating a normal coarse emulsion with medium-chain alcohols. The short to medium-chain alcohols are generally considered as cosurfactants in the microemulsion system. The presence of surfactant and optionally cosurfactant in the system makes the interfacial tension very low. Therefore, the microemulsion is thermodynamically stable and forms spontaneously, with an average droplet diameter of 1 to 100 $\mu$m.[7-9] An "oil-in-water microemulsion" is a microemulsion wherein the concentration of water exceeds the concentration of oil on a molar basis. A "deparaffinizing microemulsion" is a special subset comprising an oil-in-water system having a substantial amount of stabilizing surfactant. The oil component of a deparaffinizing microemulsion is a paraffin solvent, meaning that when the microemulsion contacts the paraffin in a paraffin-embedded biological sample, the paraffin is solubilized by the oil. The oil is generally referred to herein as a nonpolar organic solvent, but the terms are used interchangeably throughout.

An "exchanging composition" is a surfactant:water, surfactant:oil, or surfactant:oil:water composition, optionally comprising a cosurfactant, capable of removing residual nonpolar organic solvent from the deparaffinized slide. Preferred surfactant:water compositions are approximately 20% by weight nonionic detergent in water, such as TOMADOL™ 1-73B (Tomah Inc., Milton, Wis.) and TERGITOL™ 15-S-7 (SigmaAldrich Inc., St. Louis, Mo.).

Other exchanging compositions of a surfactant:oil composition have the capability of exchanging oil for water, or water for oil. Several compositions are demonstrated herein in Table 1.

TABLE 1

| Composition | Surfactant type, amount | Oil amount |
| --- | --- | --- |
| 1 | TOMADOL ™ 1-73B (4 grams) | NORPAR15 (1 gram) |
| 2 | COLAMULSE ™ FE (4 grams) | NORPAR15 (1 gram) |

TABLE 1-continued

| Composition | Surfactant type, amount | Oil amount |
|---|---|---|
| 3 | TOMADOL ™ 1-5 (4 grams) | NORPAR15 (1 gram) |
| 4 | TOMADOL ™ 91-6 (4 grams) | NORPAR15 (1 gram) |
| 5 | TERGITOL ™ 15-S-7 (4 grams) | NORPAR15 (1 gram) |

The exchanging compositions enable a method of exchanging oil-for-water in a tissue sample predominantly containing oil comprising contacting the tissue sample with an exchanging composition comprising a surfactant in oil wherein the surfactant is also soluble in water. Surprisingly, compositions 1-5 may also be used in the reverse manner, that is, to exchange water-for-oil in a tissue sample predominantly containing water.

Biological samples include any tissue section, artificial cell line embedded in paraffin, paraffin/agar or other paraffin-based medium. Paraffin-based embedding media are well-known to one of ordinary skill in the art of histotechnology.

A "solubility test" for purposes of determining surfactant solubility in nonpolar organic solvent is performed by adding about 0.5 gram of surfactant to about 10 grams of nonpolar solvent and mixing or vortexing the mixture for about 10 to about 30 sec; a transparent or translucent mixture indicates mutual miscibility. A "solubility test" for purposes of determining surfactant solubility in water is performed by adding about 0.5 gram of surfactant to about 10 grams of water and mixing or vortexing the mixture for in about 10 to about 30 sec; a transparent or translucent mixture indicates mutual miscibility. Viscosity of the mixtures may increase, but does not affect their visual clarity. The solubility test should be performed at the working temperature of the intended deparaffinizing process, typically about 15 C. to about 50 C. Mutual solubility of the surfactant in both water and oil is indicated using these tests A "Nonpolar organic solvent" is a nonpolar hydrocarbon or mixture of hydrocarbons (e.g. as from a petroleum distillate) that has a boiling point well above room temperature of 25 C., preferably above 110 C., more preferably from about 140 C. to about 250 C., that is in liquid phase at the temperatures used with the present invention (usually 15 to 50 degrees C.) and that is capable of dissolving paraffin used for embedding biological specimens. The nonpolar organic solvent can be a complex mixture of long-chain linear and branched alkane hydrocarbons containing for example esters of fatty acids and higher glycols. The solubility of paraffin in the solvent at 25 C. is typically at least 0.1 gram paraffin per 1 liter of solvent, preferably 0.1 gram per 100 ml of solvent, more preferably; 0.1 gram per 10 ml of solvent, and most preferably capable of dissolving an amount of paraffin equal to about 50% of the solvent by solution weight. The nonpolar organic solvent is further miscible with a polar organic cosurfactant when used in a deparaffinizing microemulsion of the invention.

Examples of nonpolar organic solvents include aromatic hydrocarbons, aliphatic hydrocarbons, terpenes, other oils, and petroleum distillates. Preferred nonpolar organic solvents have little or no toxic effects. Furthermore preferred solvents are those not classified by the Environmental Protection Agency as hazardous waste. A preferred paraffin-solubilizing solvent furthermore has a flash point higher than about 60 C. which minimizes flammability. A preferred solvent furthermore lacks toxicity, carcinogenicity, and corrosiveness. An isoparaffinic hydrocarbon is an example of a preferred paraffin-solubilizing solvent, in part because of its lack of toxicity, carcinogenicity, corrosiveness and flammability.[10] Preferred isoparaffins are branched aliphatic hydrocarbons with a carbon skeleton length ranging from approximately C10 to C15, or mixtures thereof. One preferred isoparaffin hydrocarbon mixture has a flashpoint of about 74 C. Another preferred paraffin-solubilizing solvent is a mixture of C10 to C50 branched or linear hydrocarbon chains having a distillation range from a boiling point of 150 C. to about 250 C., and has the general formula of $C_nH_{(2n+m)}$ where n=10-50 and m=0-4.

Particularly preferred nonpolar organic solvents include NORPAR 15, mineral spirits, or LIQUID COVERSLIP™ from Ventana. NORPAR 15 is a high (>95%) normal paraffin hydrocarbon fluid (ExxonMobil Chemical) nominally comprising linear C15, with low volatility and a high boiling point. Mineral spirits, comprising short chain linear and branched aliphatic hydrocarbons, is another preferred paraffin-solubilizing organic solvent. A preferred terpene is limonene. Other terpenes that can be used include terpins, terpinenes and terpineols. Less preferably the solvent is an aromatic hydrocarbon solvent such as an alkylbenzene, e.g. toluene, or a dialkylbenzene, e.g. xylene. Toluene and xylene are less preferred because of their toxicity and rating as hazardous waste. Furthermore, as discussed below, even when xylene or toluene are used in embodiments of the invention, subsequent alcohol washes are eliminated and replaced with a non-hazardous aqueous wash solution.

A "polar organic cosurfactant" or "cosurfactant" comprises polar organic solvents that are individually soluble in water and in oil, and includes ketones and lower alcohols, which include polyhydroxy alcohols, diols, and glycols, and lower ethers. Preferred alcohols and diols are C2 to C8 alcohols and diols. Most preferred are ethanol, ethylene glycol, propanol, isopropanol, butanol, tert butanol, propylene glycol, hexanediol, octanediol, and mixtures thereof. A preferred ketone solvent is typically C3 to C5 ketone. Most preferred ketone solvents are acetone and methyl ethyl ketone. Preferred ethers are C2 to C6 ethers. Particularly preferred polar organic cosurfactants are selected from the group consisting of methanol, ethanol, isopropanol, butanol, tert-butanol, allyl alcohol, acetone, ethylene glycol, propylene glycol, hexanediol, octanediol, and mixtures thereof. Acetonitrile, dimethylsulfoxide, and dimethylformamide are less preferred polar organic cosurfactants. Furthermore, the polar organic cosurfactant can be a mixture of polar organic solvents. The cosurfactant is preferably soluble in both oil and water.

A "surfactant" comprises a compound with a molecular structure comprising a hydrophilic portion that is miscible with water, and a lipophilic portion that is miscible with nonpolar organic solvent. Surfactants that can be used in compositions of the invention include polyethylene glycol-based nonionic surfactants of the formula $$R_1-X-(CH_2CH_2O)_n-R_2$$

wherein R1 is a long-chain linear or branched alkane hydrocarbon from about C4 to about C20; X is a linking group comprising an ether, ester, carbonate, benzyl, or sorbitol; n is from about 5 to about 30; and R2 is a hydrogen. R1 may alternatively comprise polypropylene oxide, polysiloxane, or a fluoroalkane. R2 may alternatively comprise linear or branched alkane hydrocarbon from about C1 to about C20, an alkyl carboxylic acid, an alkyl sulfonate, an alkyl amine, an alkyl amine oxide, an alkyl quaternary amine, polypropylene oxide, polysiloxane, or a fluoroalkane.

Preferred surfactants of this formula are individually soluble in both nonpolar organic solvent and water. Examples of preferred nonionic surfactants include ethylene oxide condensates of linear fatty alcohols (e.g., sold under the tradename TOMADOL™), ethylene oxide condensates of branched fatty alcohols (e.g., sold under the tradenames TOMADOL™ TOMADYNE™, TERGITOL™, and MERPOL™), and ethylene oxide condensates of linear fatty acids (e.g., sold under the tradename COLAMULSE™), and blends thereof Particularly preferred surfactants include Tomadols 1-5, 91-6, 1-7, 23-6.5, 91-8, 900, and 1-73B (Tomah Inc.; Milton, Wis.); TOMADYNE™ dL (Tomah Inc.; Milton, Wis.); Tergitols15-S-7 and 15-S-9 (SigmaAldrich Inc., St. Louis, Mo.); Merpols S H and O J (SigmaAldrich Inc., St. Louis, Mo.); polyethylene glycol 400 laurate ("COLAMULSE™ FE"; Colonial Inc., South Pittsburg, Tenn.); and hexaethylene glycol tridecane ether (SigmaAldrich Inc., St. Louis, Mo.).

Deparaffinizing microemulsions of this invention comprise surfactant, oil, and water, wherein the weight percentage of surfactant is from about 5% to about 90%, the weight percentage of oil is from about 5% to about 90%, and the weight percentage of water is from 0% to about 90%. A preferred embodiment comprises Composition A (TOMADOL™ 96-1, NORPAR 15 and water in a 4:1:1 ratio, respectively, by weight, or respective weight percentages of 67%/16.5%/16.5%).

Exchanging compositions of this invention comprise surfactant, oil and water, and optionally a cosurfactant, wherein the weight percentage of surfactant is from about 5% to about 95%, the weight percentage of oil is from 0% to about 95%, the weight percentage of water is from 0% to about 95%, and the weight percentage of the cosurfactant is from 0% to about 50%. A preferred embodiment comprises Composition B (TOMADYNE™ dL: NORPAR 15:water) at a ratio of 5:1:5 by weight (or respective weight percentages of 45.5%/9%/45.5%). Another preferred composition is Composition C (TOMADOL™ 1-73B: NORPAR 15:water:isopropanol) at a ratio of 4:1:1:0.5 by weight (or respective weight percentages of 62%/15%/15%/8%).

The following examples are illustrations of the embodiments of the inventions discussed herein, and should not be applied so as to limit the appended claims in any manner.

Example 1

One-Step Deparaffinizing with Deparaffinizing Composition A

Several paraffin-embedded tissue specimens (4-micron sections from different paraffin-embedded blocks mounted on SUPERFROST PLUS™ microscope slides (Erie Scientific, Portsmouth, N.H.) were deparaffinized according to the following protocol. Composition A was made by weighing out 4 grams of 91-6 surfactant, adding 1 gram of NORPAR15, mixing, then adding 1 gram of water with mixing to produce a clear solution. Each slide was then loaded onto a DISCOVERY® automated slide stainer (Ventana Medical Systems, Inc., Tucson, Ariz.) and the temperature was programmed to 45 C. Deparaffinizing Composition A was contacted with the tissue section by manually applying 1.0 ml of the microemulsion to substantially cover the tissue and entire glass surface without it wicking off the edge of the slide. The slide and sample were incubated at temperature for four minutes. The slide was then washed two times with EZ PREP™ (PN 950-102, Ventana), a surfactant-containing buffer, to remove the microemulsion. Slides were then washed under gentle tap water and a glass coverslip applied in preparation for visual inspection. The slide was held up in room lighting and viewed for phantom residual paraffin. In addition, visual inspection was performed with brightfield magnification, as well as polarized light, which is particularly effective for visualizing any residual paraffin. Occasionally residual oiliness was observed on the slides with certain paraffin block samples, perhaps due to small amounts of impurities within the paraffin. This residual oiliness was not observed by increasing the time at 45 C., or increasing the number of applications of microemulsion. In place of manually applying the 1.0 ml volume of the composition, it is envisioned that this material could be added to the existing plumbing of any number of automated dispensing systems.

Example 2

Two-Step Deparaffinizing with Exchanging Composition B

Several paraffin-embedded tissue specimens of approximately 4 microns thickness each from different paraffin-embedded blocks mounted on SUPERFROST PLUS™ slides were deparaffinized according to the following protocol. The slide were first loaded onto a DISCOVERY® (Ventana Medical Systems, Inc., Tucson, Ariz.) automated slide stainer and the temperature was programmed to 45 C. Pure LIQUID COVERSLIP™ (Ventana) was first applied automatically using the DISCOVERY instrument. LIQUID COVERSLIP was incubated over the tissue section to dissolve the paraffin for two minutes at temperature. The section was then rinsed with DISCOVERY EZ PREP™ (Ventana), a surfactant-containing buffer, to rinse off the majority of the LIQUID COVERSLIP. Exchanging Composition B (TOMADYNE™ dL: NORPAR 15:water) at a weight ratio of 5:1:5, respectively, was made by weighing out 5 grams of TOMADYNE™ dL surfactant, adding 1 gram of NORPAR15, mixing, then adding 5 grams of water with mixing to produce a clear solution. Exchanging Composition B was next contacted with the deparaffinized tissue section by manually applying 1.0 ml of the microemulsion to substantially cover the tissue and glass surface without it wicking off the edge of the slide. The slide and sample were incubated at temperature for two minutes. The slide was then rinsed two times with EZ PREP™, to remove the microemulsion. Slides were inspected for residual wax or oiliness, as described in Example 1. The slides exhibited essentially no residues.

Example 3

Two-Step Deparaffinizing with Exchanging Composition C

Paraffin-embedded tissue specimens of 4 micron thickness mounted on SUPERFROST PLUS™ microscope slides were deparaffinized according to the following protocol. Two ml of NORPAR15 was applied manually over the tissue section to dissolve the paraffin for four minutes at 25 C. The slide was then drained onto an absorbent towel to rinse off excess NORPAR15. Exchanging Composition C (TOMADOL™ 1-73B: NORPAR15: water:isopropanol at a weight ratio of 4:1:1:0.5, respectively), was made by dissolving 4 grams of TOMADOL™ 1-73B in 1 gram of NORPAR15, adding 1 gram of water with mixing to produce a clear solution, and adding 0.5 gram of isopropanol with mixing to produce a clear solution. Exchanging Composition C was next contacted with the deparaffinized tissue section by manually applying the microemulsion to substantially cover the tissue without it wicking off the edge of the slide, approximately 2 ml. The slide and sample were incubated at 25 C. for four minutes. The slide was then rinsed with gently flowing tap water at 25 C. to remove the microemulsion; no gel formation was observed. The slide and sample were air dried, and demonstrated removal of the paraffin wax with no residual oiliness.

Example 4

Additional Exchanging Compositions D-I

Exchanging Composition D (TERGITOL™ 15-S-7:NORPAR15:water:isopropanol at a ratio of 4:1:1:0.25, respectively) was made by dissolving 4 grams of TERGITOL™ 15-S-7 in 1 gram of NORPAR15, adding 1 gram of water with mixing to produce a clear solution, and adding 0.25 gram of isopropanol with mixing to produce a clear solution.

Exchanging Composition E (COLAMULSE™ FE:NORPAR15:water:isopropanol) at a ratio of 4:1;1:0.25, respectively, was made by dissolving 4 grams of COLAMULSE™ FE in 1 gram of NORPAR15, adding 1 gram of water with mixing to produce a clear solution, and adding 0.25 gram of isopropanol with mixing to produce a clear solution.

Exchanging Composition F (TOMADOL™ 900:NORPAR15:water:isopropanol at a ratio of 4:1;1:0.5, respectively) was made by dissolving 4 grams of TOMADOL™ 900 in 1 gram of NORPAR15, adding 1 gram of water with mixing to produce a clear solution, and adding 0.5 gram of isopropanol with mixing to produce a clear solution.

Exchanging Composition G (TERGITOL™ 15-S-9:NORPAR15:water:isopropanol at a ratio of 4:1;1:1.25, respectively) was made by dissolving 4 grams of TERGITOL™ 15-S-9 in 1 gram of NORPAR15, adding 1 gram of water with mixing to produce a clear solution, and adding 1.25 gram of isopropanol with mixing to produce a clear solution.

Exchanging Composition H (TOMADOL™ 91-6:NORPAR15:water:isopropanol at a ratio of 4:1;1:0.5, respectively) was made by dissolving 4 grams of TOMADOL™ 91-6 in 1 gram of NORPAR15, adding 1 gram of water with mixing to produce a clear solution, and adding 0.5 gram of isopropanol with mixing to produce a clear solution.

Exchanging Composition I (TOMADOL™ 23-6.5:NORPAR15:water:isopropanol at a ratio of 4:1;1:1, respectively) was made by dissolving 4 grams of TOMADOL™ 23-6 in 1 gram of NORPAR15, adding 1 gram of water with mixing to produce a clear solution, and adding 1 gram of isopropanol with mixing to produce a clear solution.

Example 5

Two-Step Deparaffinizing with Exchanging Compositions D-I

Deparaffinization of paraffin-embedded tissue specimens using NORPAR15 followed by Exchanging Compositions D through I of Example 4, was performed using the protocol of Example 3. All Exchanging Compositions demonstrated no gel formation upon tap water rinsing, and all Exchanging Compositions demonstrated removal of the paraffin wax from the microscope slides with no residual oiliness.

Example 6

Two-Step Deparaffinization with Exchanging Compositions J & K

Paraffin-embedded tissue specimens having 4-micron thickness mounted on SUPERFROST PLUS™ microscope slides were deparaffinized according to the following protocol. The slide was first loaded onto a DISCOVERY automated slide stainer and the temperature was programmed to 55 C. Pure LIQUID COVERSLIP™ (Ventana) was first applied automatically using the DISCOVERY instrument. LIQUID COVERSLIP was incubated over the tissue section to dissolve the paraffin for two minutes at temperature. The section was then rinsed with REACTION BUFFER™ (Ventana) to rinse off the bulk of the LIQUID COVERSLIP. Two Exchanging Compositions J (TOMADOL™ 1-73B:water), and K (TERGITOL™ 15-S-7:water) at a surfactant:water weight ratio of 1:4 by weight, respectively, were made by dissolving the respective surfactants in the water and stirring until clear. Both of these compositions individually were next contacted with the deparaffinized tissue section by applying 1.0 ml of the surfactant:water mix. The slide and sample were incubated at temperature for two minutes to remove the residual LIQUID COVERSLIP. The slide was then rinsed two times with standard automated "DUAL RINSE" of REACTION BUFFER to remove the surfactant:water mix. Upon inspection, no residual oil or wax were observed.

Example 7

Additional Exchanging Compositions L-P

The following examples of oil-to-water and water-to-oil Exchanging Compositions are presented by way of illustration. These examples are capable of two-way exchange, that is they are capable of exchanging oil-to-water and of exchanging water-to-oil.

Exchanging Composition L was prepared by mixing TOMADOL™ 1-73B (4 grams) and NORPAR15 (1 gram) until clear.

Exchanging Composition M was prepared by mixing COLAMULSE™ FE (4 grams) and NORPAR15 (1 gram) until clear.

Exchanging Composition N was prepared by mixing TOMADOL™ 1-5 (4 grams) and NORPAR15 (1 gram) until clear.

Exchanging Composition O was prepared by mixing TOMADOL™ 91-6 (4 grams) and NORPAR15 (1 gram) until clear.

Exchanging Composition P was prepared by mixing TERGITOL™ 15-S-7 (4 grams) and NORPAR15 (1 gram) until clear.

Example 8

Exchange of Oil for Water

The exchanger compositions of Example 7 were examined for their ability to exchange oil on a slide for water, without the use of intermediate alcoholic solutions. Approximately 0.5 ml of LIQUID COVERSLIP was applied to bare SUPERFROST PLUS™ slides, i.e. they did not contain tissue samples, to substantially cover the surfaces of the slides. The excess oil was then removed by tilting the slides and draining onto an absorbent towel. Approximately 1 ml of Exchanging Compositions L-P was applied to the slides individually, to substantially cover the surface of each slide without the composition wicking off the edge. The slides were incubated at 25 C. for 4 minutes. The excess compositions were then removed by tilting the slides and draining onto an absorbent towel. The slides were individually immersed in about 250 ml of water, 25 C., for 4 min; no gel formation was observed. The slides were removed, coverslipped, and examined under 40× polarized microscope. All compositions demonstrated no oiliness. In contrast, a slide exchanged without the use of Exchanging Compositions L-P, i.e. the slide was covered with about 0.5 ml of LIQUID COVERSLIP, drained onto an absorbent towel, immersed in about 250 ml of water at 25 C. for 4 min, removed and coverslipped, demonstrated significant oily droplets in the film layer trapped between the coverslip and the slide.

Example 9

Exchange of Water for Oil

The Exchanging Compositions of Example 7 were examined for their ability to exchange water on a slide for oil, without the use of intermediate alcoholic solutions. Approximately 0.5 ml of water was applied to bare SUPERFROST PLUS™ slides, i.e. they did not contain tissue samples, to substantially cover the surfaces of the slides. The excess water was then removed by tilting the slides and draining onto an absorbent towel. Approximately 1 ml of Exchanging Compositions L-P was applied to the slides individually, to substantially cover the surface of each slide without it wicking off the edge. The slides were incubated at 25 C. for 4 minutes. The excess exchanger compositions were then removed by tilting the slides and draining onto an absorbent towel. The slides were individually immersed in about 40 ml of LIQUID COVERSLIP, 25 C., for 4 min; no to very little gel formation was observed. The slides were removed, coverslipped, and examined under 40× polarized microscope. All compositions demonstrated only trace amounts of residual water in the liquid film trapped between the coverslip and the slide. In contrast, a slide exchanged without the use of Exchanging Compositions L-P, i.e. the slide was covered with about 0.5 ml of water, drained onto an absorbent towel, immersed in about 40 ml of LIQUID COVERSLIP at 25 C. for 4 min, removed and coverslipped, demonstrated significant watery droplets in the film layer trapped between the coverslip and the slide.

It will be understood that various modifications may be made to the embodiments disclosed herein. Therefore, the above description should not be construed as limiting, but merely as exemplifications of preferred embodiments. Those skilled in the art will envision other modifications that come within the scope and spirit of the claims appended hereto. All patents and references cited herein are explicitly incorporated by reference in their entirety.

REFERENCES CITED

1. Attwood D: Microemulsions, in Kreuter H (ed): Colloidal Drug Delivery Systems. New York, Marcel Decker, 1994, p 31.
2. Ogino K, Abe M: Microemulsion formation with some typical surfactants, in Matijevic E (ed): Surface and Colloid Science. New York, Plenum Press, 1993, p 85.
3. Paul B K, Moulik S P: Microemulsions: An overview. J Disp Sci 18(4):301, 1997.
4. Tenjarla S N: Microemulsions: An overview and pharmaceutical applications. Critical Reviews™ in Therapeutic Drug Carrier Systems 16:461-521, 1999.
5. Jayakrishnan A, Kalaiarasi K, Shah D O: Microemulsions: Evolving technologies for cosmetic application. J Soc Cosmetic Chem 34:335, 1983.
6. Hoar T P, Schulman J H: Transparent water-in-oil dispersions: The oleopathic hydromicelle. Nature 102,152, 1943.
7. Prince: Microemulsions, in Theory and Practice. New York, Academic Press, 1977.
8. Prince: Microemulsions. J Soc Cosmetic Chem 21:193, 1970.
9. Baviere, et al: The influence of alcohols on microemulsion composition. J Colloid lilted Sci 81:266, 1981.
10. Mullin et al. "Toxicology update isoparaffinic hydrocarbons: a summary of physical properties, toxicity studies and human exposure data," J. App. Toxicol.10: 135-42 (1990).

We claim:

1. A method of treating a slide having a biological tissue deposited thereon to replace oil on the slide with water, the method comprising;
   (a) contacting the oil on the slide with an exchanging composition, wherein the exchanging composition consists essentially of a surfactant dissolved in a non-polar organic solvent thereby forming a microemulsion; and
   (b) rinsing the microemulsion from the slide with water, wherein the surfactant has the following structural formula:

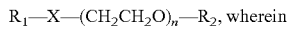

$R_1$—X—$(CH_2CH_2O)_n$—$R_2$, wherein $R_1$ is selected from the group consisting of a hydrocarbon from about C4 to about C20, a polypropylene oxide, a polysiloxane, and a fluoroalkane;
   $R_2$ is selected from the group consisting of a hydrocarbon from about C1 to C20, an alkyl carboxylic acid, an alkyl sulfonate, an alkyl amine, an alkyl amine oxide, an alkyl quaternary amine, a polypropylene oxide, a polysiloxane, a fluoroalkane and a hydrogen;
   X is a linking group comprising an ether, ester, carbonate, benzyl, or sorbitol; and
   n is from about 5 to about 30.

2. The method of claim 1, wherein the surfactant is selected from the group consisting of ethoxylated alkyl alcohols and ethoxylated alkyl carboxylic acids.

3. The method of claim 1, wherein $R_1$ is a long-chain linear or branched alkane hydrocarbon from about C4 to about C20; and $R_2$ is a hydrogen.

4. The method of claim 1, wherein $R_1$ is a polypropylene oxide, a polysiloxane, or a fluoroalkane; and $R_2$ is a linear or branched alkane hydrocarbon from about C1 to C20, an alkyl carboxylic acid, an alkyl sulfonate, an alkyl amine, an alkyl amine oxide, an alkyl quaternary amine, a polypropylene oxide, a polysiloxane, or a fluoroalkane.

5. The method of claim 1, wherein the surfactant is an ethylene oxide condensate of a linear fatty alcohol.

6. The method of claim 1, wherein the exchanging composition consists essentially of about 5% to about 95%, by weight, of said surfactant and about 5% to about 95%, by weight, of said non-polar organic solvent.

7. The method of claim 1, wherein the non-polar organic solvent and the oil are independently selected from the group consisting of terpenes, alkylbenzenes, aromatic solvents, normal paraffin oils and branched paraffin oils.

8. The method of claim 1, wherein the non-polar organic solvent is a mixture of hydrocarbons having a boiling point from about 140° C. to about 250° C.

9. A method of treating a slide having a biological tissue deposited thereon to replace a paraffin-based embedding medium on the slide with water, the method comprising;
   (a) contacting the paraffin-based embedding medium on the slide with an exchanging composition, wherein the exchanging composition consists essentially of a surfactant dissolved in a non-polar organic solvent thereby forming a microemulsion; and (b) rinsing the microemulsion from the slide with water, wherein the surfactant has the following structural formula:

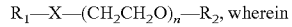
$R_1$—X—$(CH_2CH_2O)_n$—$R_2$, wherein $R_1$ is selected from the group consisting of a hydrocarbon from about C4 to about C20, a polypropylene oxide, a polysiloxane, and a fluoroalkane;

$R_2$ is selected from the group consisting of a hydrocarbon from about C1 to C20, an alkyl carboxylic acid, an alkyl sulfonate, an alkyl amine, an alkyl amine oxide, an alkyl quaternary amine, a polypropylene oxide, a polysiloxane, a fluoroalkane and a hydrogen;

X is a linking group comprising an ether, ester, carbonate, benzyl, or sorbitol; and n is from about 5 to about 30.

10. The method of claim 9, wherein the surfactant is selected from the group consisting of ethoxylated alkyl alcohols and ethoxylated alkyl carboxylic acids.

11. The method of claim 9, wherein $R_1$ is a long-chain linear or branched alkane hydrocarbon from about C4 to about C20; and $R_2$ is a hydrogen.

12. The method of claim 9, wherein $R_1$ is a polypropylene oxide, a polysiloxane, or a fluoroalkane; and $R_2$ is a linear or branched alkane hydrocarbon from about C1 to C20, an alkyl carboxylic acid, an alkyl sulfonate, an alkyl amine, an alkyl amine oxide, an alkyl quaternary amine, a polypropylene oxide, a polysiloxane, or a fluoroalkane.

13. The method of claim 9, wherein the surfactant is an ethylene oxide condensate of a linear fatty alcohol.

14. The method of claim 9, wherein the exchanging composition consists essentially of about 5% to about 95%, by weight, of said surfactant and about 5% to about 95%, by weight, of said non-polar organic solvent.

15. The method of claim 9, wherein the non-polar organic solvent is selected from the group consisting of terpenes, alkylbenzenes, aromatic solvents, normal paraffin oils and branched paraffin oils.

16. The method of claim 9, wherein the non-polar organic solvent is a mixture of hydrocarbons having a boiling point from about 140° C. to about 250° C.

\* \* \* \* \*